(12) United States Patent
Ito

(10) Patent No.: US 9,687,842 B2
(45) Date of Patent: Jun. 27, 2017

(54) SUBJECT SELECTION DEVICE AND SUBJECT SELECTION METHOD

(75) Inventor: Saburo Ito, Shizuoka-ken (JP)

(73) Assignee: Yamaha Hatsudoki Kabushiki Kaisha, Shizuoka-ken (JP)

( * ) Notice: Subject to any disclaimer, the term of this patent is extended or adjusted under 35 U.S.C. 154(b) by 241 days.

(21) Appl. No.: 14/370,053

(22) PCT Filed: Jan. 20, 2012

(86) PCT No.: PCT/JP2012/000356
§ 371 (c)(1),
(2), (4) Date: Jun. 30, 2014

(87) PCT Pub. No.: WO2013/108296
PCT Pub. Date: Jul. 25, 2013

(65) Prior Publication Data
US 2014/0370589 A1   Dec. 18, 2014

(51) Int. Cl.
*B01L 3/02* (2006.01)
*G01N 1/40* (2006.01)

(52) U.S. Cl.
CPC ..... *B01L 3/0275* (2013.01); *B01L 2200/0605* (2013.01); *B01L 2200/0647* (2013.01); *B01L 2200/0668* (2013.01); *B01L 2300/0681* (2013.01); *B01L 2300/0858* (2013.01); *B01L 2400/0605* (2013.01);

(Continued)

(58) Field of Classification Search
CPC ...... C12M 33/04; C12M 33/14; C12M 47/02; C12M 47/04; B01L 3/021; B01L 3/0275; B01L 2200/0652; B01L 2200/0668; B01L 2300/0681; B01L 2400/0605
See application file for complete search history.

(56) References Cited

U.S. PATENT DOCUMENTS 6,280,621 B1 *  8/2001 Yazawa ................. B01D 61/18
                                                  210/248
7,785,466 B1    8/2010 Smith
2004/0060859 A1 4/2004 Seshimoto et al.
(Continued)

FOREIGN PATENT DOCUMENTS

DE    19806780 C1    7/1999
JP    05-103658 A    4/1993
(Continued)

OTHER PUBLICATIONS

International Search Report; PCT/JP2012/000356; Mar. 13, 2012.
(Continued)

*Primary Examiner* — William H Beisner
(74) *Attorney, Agent, or Firm* — Studebaker & Brackett PC

(57) ABSTRACT

A suction tip includes a tip opening, a tubular passage provided with a first selector configured to permit the passage of non-selection subjects included in a collection of subjects sucked through the tip opening, and a capture portion provided on a side of the tubular passage downstream of the first selector in a suction direction of the collection of subjects and configured to capture the non-selection subjects. The capture portion includes a passage hole configured to permit the passage of the non-selection subjects and a storage portion configured to store the non-selection subjects having passed through.

7 Claims, 8 Drawing Sheets

(52) U.S. Cl.
CPC ............... *B01L 2400/0616* (2013.01); *B01L 2400/0633* (2013.01); *G01N 2001/4088* (2013.01)

(56) References Cited

U.S. PATENT DOCUMENTS

| | | |
|---|---|---|
| 2005/0214927 A1 | 9/2005 | Haley |
| 2010/0126255 A1 | 5/2010 | Norrman et al. |
| 2010/0297691 A1 | 11/2010 | Ribeiro et al. |

FOREIGN PATENT DOCUMENTS

| | | |
|---|---|---|
| JP | 07-006746 A | 1/1995 |
| JP | 2001-000178 A | 1/2001 |
| JP | 2001-161352 A | 6/2001 |
| JP | 2006-115781 A | 5/2006 |
| JP | 2009-034013 A | 2/2009 |
| JP | 2010-528611 A | 8/2010 |
| WO | 98/16312 A1 | 4/1998 |

OTHER PUBLICATIONS

The extended European search report issued by the European Patent Office on May 19, 2015, which corresponds to European Patent Application No. 12866067.7-1361 and is related to U.S. Appl. No. 14/370,053.

\* cited by examiner

FIG. 3A
FIG. 3B
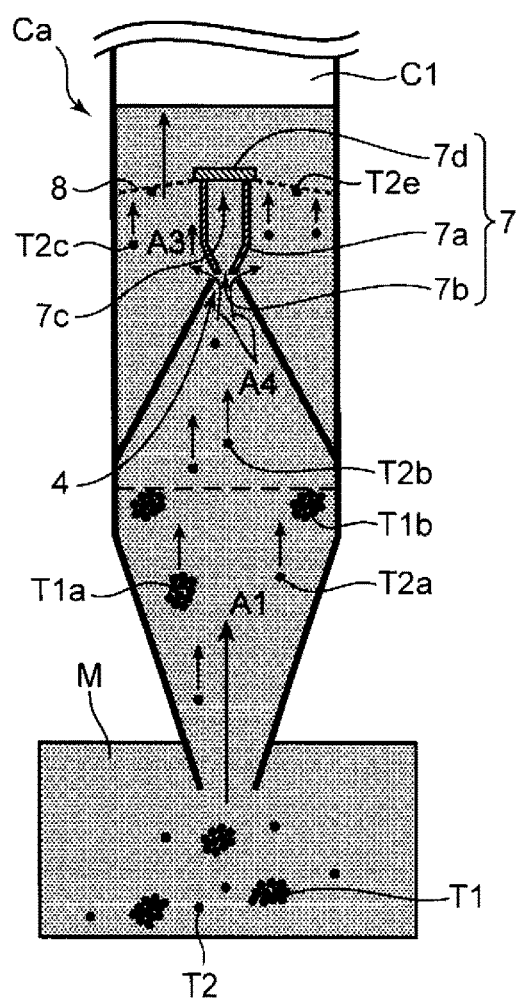
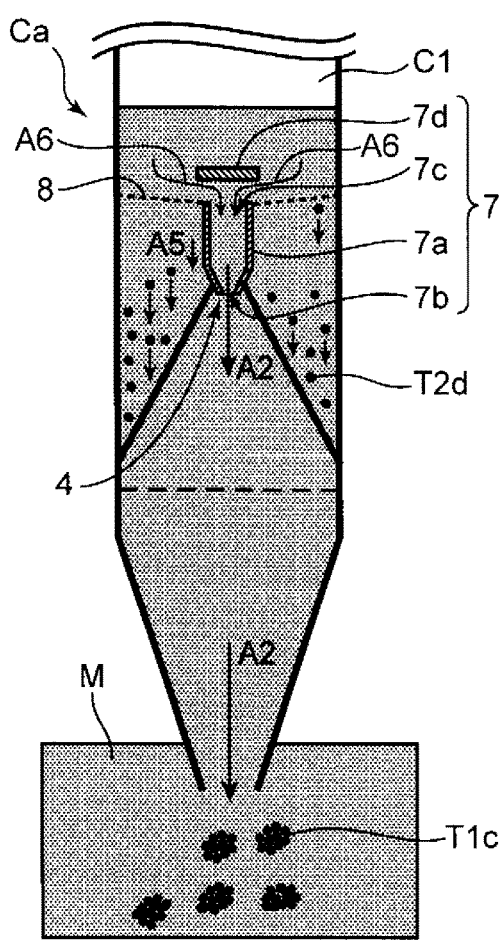

FIG. 3C
FIG. 3D
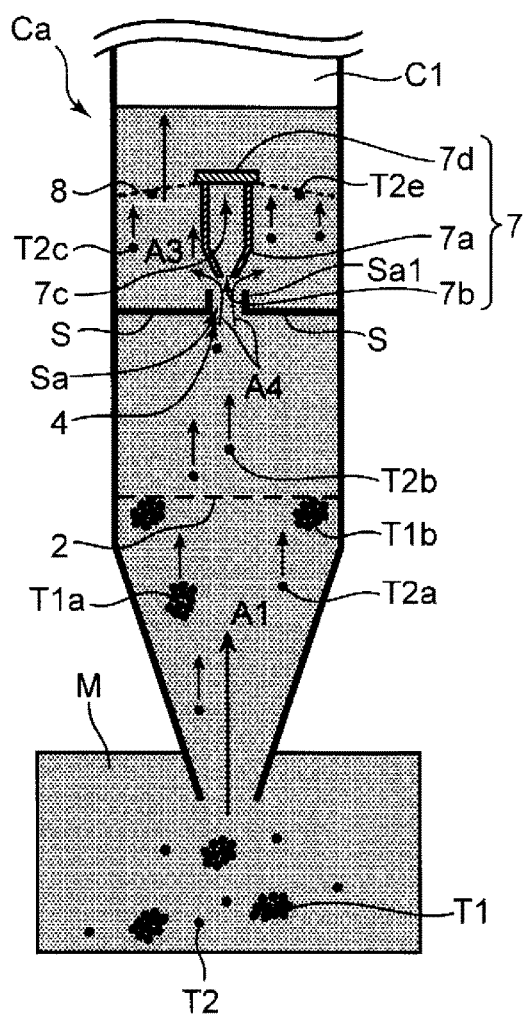
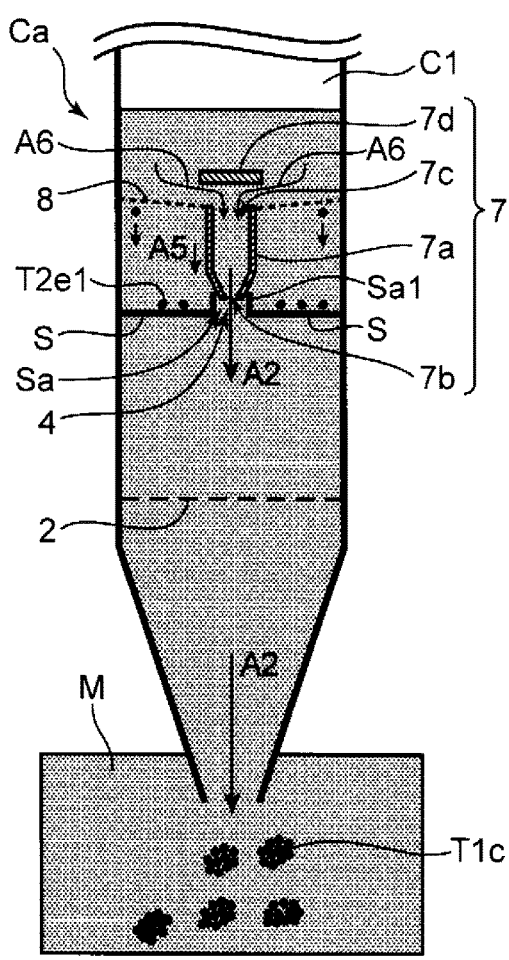

SUBJECT SELECTION DEVICE AND SUBJECT SELECTION METHOD

CROSS REFERENCE TO RELATED APPLICATIONS

This application claims benefit of priority to International Patent Application No. PCT/JP2012/000356 filed on Jan. 20, 2012, the entire content of which is incorporated herein by reference.

TECHNICAL FIELD

The present technical field relates to a suction tip. More specifically, the present disclosure relates to a suction tip capable of discharging only particles having a predetermined particle diameter or larger and storing particles having a particle diameter below the predetermined particle diameter inside in the case of sucking a collection of subjects including particles and the like of various sizes.

BACKGROUND

Conventionally, suction pipettes for sucking and measuring a fixed volume of a relatively small amount of liquid or the like have been used in various fields. Particularly, push-button type suction pipettes used with a suction tip attached to the tip are frequently used in biochemical experiments and the like. Although a suction pipette is used for sucking a fixed volume of liquid, it is also used for the purpose of moving subjects from a certain place to another as a preliminary usage.

Examples of subjects include not only liquids, but also powders, particles, cells and the like contained in liquids (hereinafter, these are referred to as a collection of subjects in some cases). These subjects such as powders have various shapes and sizes (hereinafter, these are referred to as shapes in some cases). In many cases, impurities having a small diameter are removed in advance from subjects to eliminate shape deviations of the subjects and prevent the clogging of a device used due to fine impurities. Particularly, in the fields of bio-related technology and medicine, since a large amount of impurities such as organelles and disrupted cell membranes are included in the case of using disrupted liquid of cells or the like, such impurities having a small diameter are selected and removed in an initial stage of a test.

An old method using a sieve has been known as a selection method. However, in the case of selection using a sieve or the like, there are problems of deteriorating operation efficiency and consuming rare subjects and causing contamination before and after the selection.

In view of such problems, suction tips and suction pipettes provided with a subject selection mechanism have been proposed. Japanese Unexamined Patent Publication No. 2009-34013 discloses a suction pipette in which a cup-shaped storage portion including an opening with a predetermined opening area is provided around a nozzle for sucking subjects. This suction pipette sucks and selects subjects having a diameter smaller than the opening area. Japanese Unexamined Patent Publication No. 2006-115781 discloses a filter unit which can be used for a suction pipette and in which a film filter is mountable. The filter unit of Japanese Unexamined Patent Publication No. 2006-115781 is used by being mounted in a pipette tip of a suction pipette and filters cells and the like from subjects by the thin film filter mounted inside.

SUMMARY

However, the pipette of Japanese Unexamined Patent Publication No. 2009-34013 has a problem that subjects having a small diameter cannot be removed although subjects having a diameter larger than the opening area of the storage portion can be removed. Further, the unit of Japanese Unexamined Patent Publication No. 2006-115781 has a problem that the filter needs to be removed in discharging cells and the like having a desired shape, which takes time and labor and causes contamination.

The present disclosure was developed in view of such conventional problems and aims to provide a suction tip capable of removing impurities having a diameter smaller than a desired diameter and preventing the occurrence of contamination before and after operations only by performing a series of simple operations including suction and discharge.

A suction pipette according to one aspect of the present disclosure includes a tip opening configured to suck or discharge a collection of subjects including selection subjects and non-selection subjects, a tubular passage provided with a first selector configured to select the selection subjects and the non-selection subjects included in the collection of subjects sucked through the tip opening and permit the passage of the non-selection subjects, and a capture portion provided on a side of the tubular passage downstream of the first selector in a suction direction of the collection of subjects and configured to capture the non-selection subjects, and the capture portion includes a passage hole configured to permit the passage of the non-selection subjects and a storage portion configured to store the non-selection subjects having passed through the passage hole.

An object, features and advantages of the present disclosure will become more apparent upon reading the following detailed description along with the accompanying drawings.

BRIEF DESCRIPTION OF THE DRAWINGS

FIG. 3A is a diagram showing a suction operation using a suction tip according to a second embodiment of the present disclosure.

FIG. 3B is a diagram showing a discharge operation using the suction tip according to the second embodiment of the present disclosure.

FIG. 3C is a diagram showing a suction operation using a suction tip according to another example of the second embodiment of the present disclosure.

FIG. 3D is a diagram showing a discharge operation using the suction tip according to the other example of the second embodiment of the present disclosure.

DETAILED DESCRIPTION

First Embodiment

Figure 1:
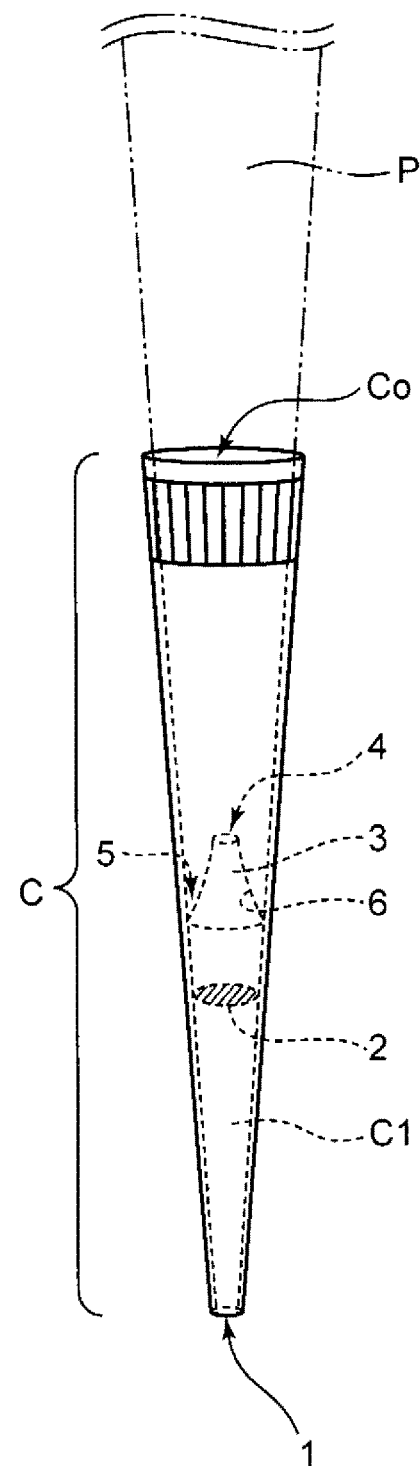
FIG. 1 is a diagram showing the configuration of a suction tip according to a first embodiment of the present disclosure.

Hereinafter, a suction tip of a first embodiment of the present disclosure is described in detail with reference to the drawings. FIG. 1 is a diagram showing the configuration of the suction tip according to the first embodiment of the present disclosure.

Suction Tip C

A suction tip C is an experimental tool which is used by being attached to a suction pipette P, which is one type of a suction device, and provided with a tubular passage C1 for sucking subjects and temporarily holding the sucked subjects when a user sucks the subjects by operating the suction pipette P. Note that the suction pipette P is a suction device having a tip part which enters an opening Co of the suction tip C. The suction pipette P sucks the subjects by generating a suction force from a tip opening 1 of the suction tip C by the user operating a push button (not shown) with the suction tip C attached.

As shown in FIG. 1, the suction tip C of this embodiment includes the tip opening 1, the tubular passage C1 provided with a first film filter 2 (first selector) and a conical member 3. Each component is described in detail later.

The size (inner volume) of the suction tip C is not particularly limited and the suction tip C having an inner volume of, e.g. about 1 µL to 5 mL can be appropriately used.

The thickness of a tube wall of the suction tip C is not particularly limited, but is preferably about 100 to 600 µm since strength decreases if the tube wall is too thin.

A material for the suction tip C is not particularly limited provided that it is a material used for ordinary suction tips. For example, a resin such as polypropylene or polystyrene or the like can be adopted as the material.

A method for fabricating the suction tip C is not particularly limited and a conventionally known method for fabricating a suction tip can be adopted. For example, a molding method for melting the above material and injecting it into a forming mold can be adopted.

Collection of Subjects M

A collection of subjects M includes selection subjects T1 and non-selection subjects T2. The type of the collection of subjects M is not particularly limited, but examples thereof include mixtures of particles having various shapes and particle diameters, cell culture solutions and cell treatment solutions containing cells and impurities having various sizes. For example, if the collection of subjects M is a mixed slurry of particles having various shapes and particles having a predetermined shape are sucked and discharged using the suction tip C, the discharged particles fall under the selection subjects T1. Similarly, if the collection of subjects M is a cell culture solution or a cell treatment solution including cells and impurities having various sizes and only cells having a predetermined shape are sucked and discharged using the suction tip C, the discharged cells having the predetermined shape fall under the selection subjects T1.

The selection subjects T1 to be sucked using the suction tip C of this embodiment are preferably bio-based cells and more preferably bio-based cell aggregates.

If the suction tip C of this embodiment is used for bio-based cells as subjects, only cells having a diameter larger than a predetermined diameter can be extracted as the selection subjects T1 from the collection of subjects M only by performing a series of suction and discharge operations. At that time, since a disassembling operation such as the removal of the first film filter 2, to be described later, is not necessary, the user can efficiently perform the operations without causing contamination in the fields of bio-related technology and medicine in which contamination is particularly problematic.

A bio-based (also derived from a cell strain) cell aggregate (spheroid) is generally formed by aggregating several to several hundred thousands of individual cells. Cell aggregates have various shapes such as substantially spherical, substantially rectangular, tubular and irregular shapes. A test result obtained using such a cell aggregate derived from a cell strain considers functions of individual cells as compared with a test result obtained using one cell since a biosimilar environment considering interactions among cells is reconfigured in the cell aggregate, and experiment conditions can be made uniform in accordance with an environment in a biological body. As described above, if the suction tip C of this embodiment is used, only cell aggregates having a diameter larger than the predetermined diameter can be extracted as the selection subjects T1 from the collection of subjects M only by performing a series of suction and discharge operations. Thus, a highly reliable result can be obtained in the fields of bio-related technology and medicine since the suction tip C of this embodiment can easily eliminate cell aggregates and the like having distorted shapes.

Tip Opening 1

The tip opening 1 is an opening for sucking or discharging the collection of subjects M (see FIG. 2A) including the selection subjects T1 and non-selection subjects T2 by the user operating the suction device such as the suction pipette attached with the suction tip C, and formed as an end opening of the tubular passage C1 provided with an inner peripheral wall having a substantially circular cross-section on a tip part of the suction tip C. The user immerses at least the tip opening 1 in a container storing the collection of subjects M and sucks the collection of subjects M by operating the suction device such as the suction pipette P.

An opening area of the tip opening 1 has only to be larger than diameters of the selection subjects T1 and may be appropriately adjusted in accordance with the diameters of the selection subjects T1 to be sucked. For example, if the sizes of the cell aggregates are 300 to 500 µm when the cell aggregates are selected as selection subjects T1 as described above, a diameter of the tip opening 1 has only to be about 150 to 1000 µm.

Note that the shape of the tip opening 1 of the suction tip C of this embodiment may be other than the circular shape and is not particularly limited. An optimal shape can be appropriately adopted as the shape of the tip opening 1 in accordance with the shapes of subjects. For example, when bar-like particles are selected as the selection subjects T1 besides substantially spherical cell aggregates, the user can prevent large spherical particles and flat particles from being sucked through the tip opening 1 by using the suction tip C with the tip opening 1 having a narrow shape.

Tubular Passage C1

The collection of subjects M passes through the tubular passage C1 when being sucked using the suction device such as the suction pipette P. As shown in FIG. 1, the tubular passage C1 is a passage formed inside the suction tip C and the tip opening 1 is formed on a tip part.

A diameter of the tubular passage C1 is not particularly limited and has only to be a size which enables the passage of the subjects. For example if the sizes of the cell aggregates are 300 to 500 μm when the cell aggregates are selected as the selection subjects T1, the diameter of the tubular passage C1 has only to be about 400 to 2000 μm.

The sucked collection of subjects M moves in the tubular passage C1 toward a downstream side in a suction direction (hereinafter, may be merely referred to as in the suction direction in some cases) while the user performs the suction operation by operating the suction pipette and moves in the tubular passage C1 toward an upward direction in the suction direction (hereinafter, may be merely referred to as in a discharge direction in some cases) while the user performs the discharge operation by operating the suction pipette. If the sucked collection of subjects M moves in the suction direction, the selection subjects T1 and the non-selection subjects T2 included in the collection of subjects M reach the first film filter 2.

First Film Filter 2

The first film filter 2 causes only the non-selection subjects T2 out of the selection subjects T1 and the non-selection subjects T2 included in the collection of subjects M to stay at a side upstream of the arrangement position of the first film filter 2 in the suction direction of the collection of subjects M by permitting the passage of only the non-selection subjects T2 sucked through the tip opening 1 without permitting the passage of the selection subjects T1. As shown in FIG. 1, the first film filter 2 is shaped in conformity with a horizontal cross-sectional shape of the tubular passage C1 and joined to an inner peripheral wall of the tubular passage C1. The first film filter 2 is arranged somewhat upstream of a central position of the suction tip C in the suction direction of the collection of subjects M.

The first film filter 2 is a porous film provided with through holes (first through holes) having a smaller diameter than those of the selection subjects T1. An opening area of the first through holes is not particularly limited. The user can adopt the first film filter 2 provided with the first through holes having an optimal opening area in accordance with the diameters of the selection subjects T1 to be selected. As an example, the diameter of the first through holes of the first film filter 2 can be set at about 100 μm when the selection subjects T1 are cell aggregates having a diameter of 300 μm.

A thickness of the first film filter 2 is not particularly limited and is, for example, about 10 to 100 μm. Since the first film filter 2 is thin as just described, it is not bulky and can be provided in the tubular passage C1 of the suction tip C. Further, even as compared with a suction tip including no first film filter 2, the inner volume is not drastically reduced. Thus, a measurement error due to a difference in inner volume does not occur in the case of using a conventional suction tip provided with the first film filter 2.

The type of the first film filter 2 is not particularly limited. For example, it is possible to use the first film filter 2 used to separate and filter a material such as protein, cells or the like. Specifically, a membrane filter using nylon, cellulose or the like as a raw material, a glass fiber filter or the like can be used.

Note that although the first film filter is a porous film in this embodiment, it is not limited to this. For example, the suction tip C of this embodiment may adopt a mesh member formed with first through holes in a lattice arrangement or a mesh member having micropores as the first film filter.

Further, the shape of the first through holes is not limited to a circular shape and may be an elliptical or polygonal shape and first through holes having these shapes may be regularly or irregularly arranged. As described above, if bio-based cell aggregates are the selection subjects T1 and the selection subjects T1 have a substantially spherical shape, it is preferable to adopt the first film filter 2 formed with the first through holes having a shape other than a circular shape so that the substantially spherical selection subjects T1 do not pass through the first through holes.

Conical Member 3

The conical member 3 (capture mechanism, capture portion) captures the non-selection subjects T2 having passed through the first film filter 2. The conical member 3 is provided downstream of the first film filter 2 in the suction direction of the collection of subjects M in the tubular passage C1. The conical member 3 includes a passage hole 4 for permitting the passage of the collection of subjects M including the non-selection subjects T2 and a storage portion 5 for storing the non-selection subjects T2 having passed through. Note that the storage portion 5 of this embodiment functions when the suction tip C is used in an upright state with the tip opening 1 facing down.

The conical member 3 includes a tapered portion 6 for narrowing a flow passage for the sucked collection of subjects M in the suction direction of the collection of subjects M. An upstream end part of the tapered portion 6 in the suction direction of the collection of subjects M is joined to the inner peripheral wall of the tubular passage C1 and the passage hole 4 for permitting the passage of the collection of subjects M including the non-selection subjects T2 is formed on a narrowed end part of the tapered portion 6.

Figure 2A:
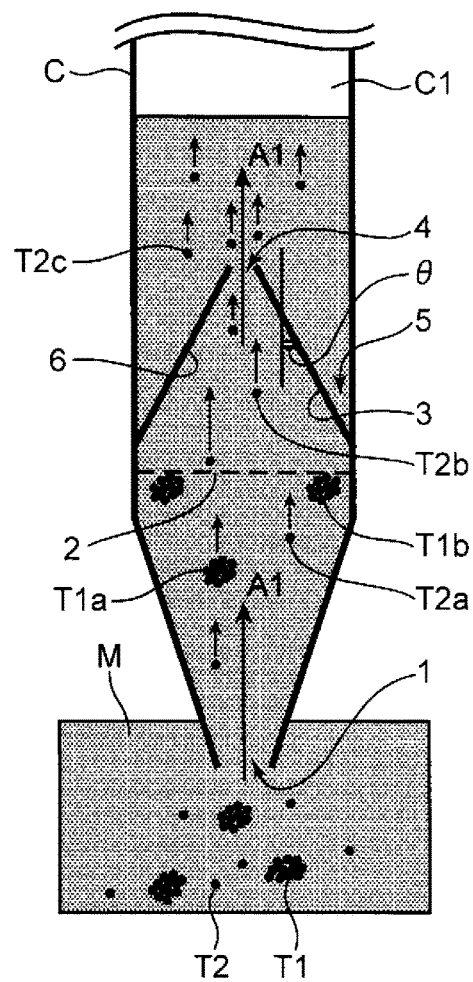
FIG. 2A is a diagram showing a suction operation using the suction tip according to the first embodiment of the present disclosure.

A rate of the tapered portion 6 narrowing the flow passage for the sucked subjects (diameter reduction rate) may be constant or varied to gradually increase in the suction direction of the collection of subjects M. Specifically, an angle of inclination θ of the tapered portion 6 may be constant as shown in FIG. 2A or may be varying.

The angle of inclination θ is preferably equal to or larger than 30° and equal to or smaller than 60°. If the angle of inclination exceeds 60°, the storage portion 5 formed between an outer peripheral wall of the conical member 3 and the inner peripheral wall of the tubular passage C1 becomes shallow and there is a possibility of being unable to sufficiently store the non-selection subjects T2. As a result, the non-selection subjects 2 that are not stored may possibly in reverse flow and be discharged through the passage hole 4. On the other hand, if the angle of inclination is below 30°, the length of the conical member 3 needs to be increased to make an opening area of the passage hole 4 formed on the end part of the tapered portion 6 of the conical member 3 small. Thus, the suction tip C becomes larger in size and convenience may be possibly deteriorated.

A material for the conical member 3 is not particularly limited. For example, resin such as polypropylene or polystyrene can be adopted as the material. Besides, metal, such as aluminum, may be formed into the conical member 3.

The passage hole 4 is formed on the narrowed end part of the tapered portion 6. The passage hole 4 is a hole through which the collection of subjects M including the non-selection subjects T2 passes. The passage hole 4 is preferably shaped such that the non-selection subjects T2 easily pass at the time of sucking the collection of subjects M and a reverse flow of the non-selection subjects T2 can be efficiently prevented at the time of discharging the collection of subjects M. Thus, a diameter of the passage hole 4 is preferably, for example, 100 to 500 µm. If the diameter of the passage hole 4 is below 50 µm, the flow of the collection of subjects M at the time of suction is excessively suppressed, wherefore the suction operation may not possibly smoothly proceed. On the other hand, if the diameter of the passage hole 4 exceeds 500 µm, the non-selection subjects T2 are mixed with the collection of subjects M and tend to flow in reverse at the time of discharging the collection of subjects M.

The shape of the passage hole 4 is not particularly limited. Various shapes such as a circular shape, an elliptical shape and a polygonal shape can be adopted as the shape of the passage hole 4.

The number of the passage hole(s) 4 is not particularly limited. Since the passage hole 4 is formed on the narrowed end part of the tapered portion 6, the passage hole 4 may be formed on each end part if the conical member 3 includes a plurality of tapered portions 6 and the plurality of tapered portions 6 form a plurality of end parts.

Figure 2B:
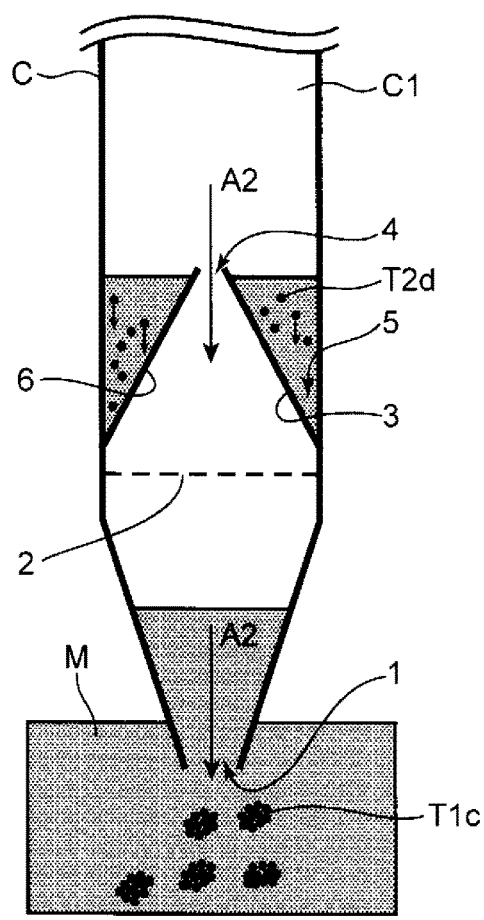
FIG. 2B is a diagram showing a discharge operation using the suction tip according to the first embodiment of the present disclosure.

The storage portion 5 stores the non-selection subjects T2 when the collection of subjects M is discharged. The storage portion 5 is a space formed between the outer peripheral wall of the conical member 3 and the inner peripheral wall of the tubular passage C1. If the collection of subjects M is discharged from the tubular passage C1 as shown in FIG. 2B, the collection of subjects M that is not discharged remains in the space between an outer peripheral wall of the tapered portion 6 and the inner peripheral wall of the tubular passage C1. The non-selection subjects T2 pass through the passage hole 4 along an inner peripheral wall of the tapered portion 6 at the time of sucking the collection of subjects M (see FIG. 2A), but substantially all the non-selection subjects T2 precipitate to the storage portion 5 along the outer peripheral wall of the tapered portion 6 to be stored therein at the time of discharge.

Figure 2C:
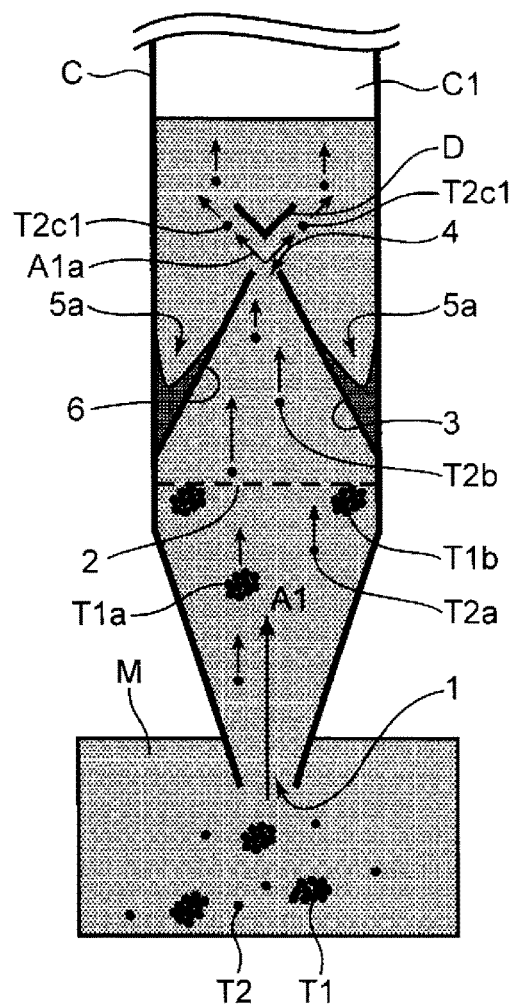
FIG. 2C is a diagram showing a suction operation using a suction tip according to another example of the first embodiment of the present disclosure.

Note that the shape of the storage portion 5 is not particularly limited. Specifically, the storage portion 5 is not limited in shape to the storage portion 5 in the form of a deep valley formed between the flat outer peripheral wall of the conical member 3 and the flat inner peripheral wall of the tubular passage C1 as shown in FIGS. 2A and 2B and may be a moderately recessed storage portion 5a formed between the outer peripheral wall of the conical member 3 and the inner peripheral wall of the tubular passage C1, for example, as shown in FIG. 2C.

The suction and discharge operations using the suction tip C of this embodiment are described with reference to FIGS. 2A and 2B. FIG. 2A is a diagram showing a state of sucking the collection of subjects M when the collection of subjects M is sucked using the suction tip C of this embodiment. FIG. 2B is a diagram showing a state of discharging the collection of subjects M when the collection of subjects M is discharged using the suction tip C of this embodiment.

If the user performs the suction operation by operating the suction pipette (not shown) as a suction device as shown in FIG. 2A, the collection of subjects M including the selection subjects T1 and the non-selection subjects T2 is sucked through the tip opening 1 and moves in the suction direction in the tubular passage C1. The collection of subjects M is stored in a container (not shown) such as a beaker. An arrow A1 indicates a moving direction of the collection of subjects M in the suction direction.

The first film filter 2 permits the passage of the non-selection subjects T2 without permitting the passage of the selection subjects T1 out of the selection subjects T1 and the non-selection subjects T2 included in the collection of subjects M arrived at the first film filter 2. Denoted by T1a are selection subjects moving in the direction A1 in the tubular passage C1, denoted by T2a are non-selection subjects moving in the direction A1 in the tubular passage C1 and denoted by T1b are selection subjects remaining in the tubular passage C1 without being able to pass through the first film filter 2.

The non-selection subjects T2 having passed through the first film filter 2 further move in the suction direction of the collection of subjects M together with the collection of subjects M having selected and removed the selection subjects T1 therefrom. Denoted by T2b are non-selection subjects having passed through the first film filter 2. The non-selection subjects T2b moving in the suction direction of the collection of subjects M move along an inclined surface of the tapered portion 6 of the conical member 3 and pass through the passage hole 4 of the conical member 3. Denoted by T2c are non-selection subjects having passed through the passage hole 4.

Subsequently, if the user performs the discharge operation by operating the suction pipette (not shown) as shown in FIG. 2B, the collection of subjects M including the non-selection subjects T2 moves in the subject discharge direction. In this case, the collection of subjects M including no non-selection subjects T2 passes through the passage hole 4, but most of the non-selection subjects T2 cannot pass through the passage hole 4 and move to the storage portion 5. Denoted by T2d are non-selection subjects moving to the storage portion 5. The collection of subjects M including no non-selection subjects T2 passes through a first film filter 2 and is discharged together with the selection subjects T1.

As just described, only the non-selection subjects T2 can be removed from the collection of subjects M and only the selection subjects T1 can be discharged by performing only a series of suction and discharge operations. The tapered portion 6 provided in the conical member 3 prompts the non-selection subjects T2 to pass through the passage hole 4 at the time of suction, but prompts them to move to the storage portion 5 at the time of discharge. Thus, the suction tip C of this embodiment can select and remove the non-selection subjects T2 with high accuracy.

Note that although the suction tip C integrally provided with the first film filter 2 and the conical member 3 is described as an example in this embodiment, the first film filter 2 and the conical member 3 can be prepared as separate members. Specifically, a filter unit provided with the first film filter 2 and a capture unit provided with the conical member 3 can be separately prepared and can be assembled by being fitted into or bonded to a conventional suction tip.

As described above, the suction tip C of this embodiment can discharge the selection subjects T1 having a larger diameter than the non-selection subjects T2 by the suction and discharge operations. Thus, the necessary selection subjects T1 are not left in the suction tip C after the discharge, wherefore the user need not disassemble the suction tip C and does not cause contamination.

Note that although the suction tip C is preferably disposable after being assembled from various units described above and used, it is also possible to reuse the suction tip C such as by disassembling and cleaning it. In such a case, it is preferable to sterilize various units by alcohol sterilization, UV irradiation, high-pressure steam sterilization or the like before the reuse to prevent contamination.

Further, although the operation in discharging the collection of subjects M is described with reference to FIG. 2B in this embodiment, the user can cause only the selection subjects T1 to precipitate through the tip opening 1 and extract them even without prompting the discharge such as by pushing down a push button (not shown) of the suction pipette.

Specifically, when the suction operation is finished, the selection subjects T1 introduced into the tubular passage C1 start precipitating in a direction of gravity. In a state where the tip opening 1 is immersed in the liquid, no surface tension acts on the tip opening 1 unlike a case where the tip opening 1 is exposed to outside air. Thus, the selection subjects T1 fall from the tip opening 1 even if the user does not perform the discharge operation.

At that time, the non-selection subjects T2c having passed through the passage hole 4 may possibly pass through the passage hole 4 again since they also precipitate in the direction of gravity. Thus, the user preferably prompts the non-selection subjects T2c to precipitate to the storage portion 5 without permitting the passage thereof through the passage hole 4, for example, by inclining the suction tip C.

Note that although the suction tip C of this embodiment can sufficiently select the selection subjects T1 only by performing a series of suction and discharge operations only once as described above, the number of times of the operations are not limited to once and the operations may be performed a plurality of times. For example, after the collection of subjects M before the selection is transferred from a container (not shown) storing the collection of subjects M to another container by operating the suction pipette P attached with the suction tip C of this embodiment, the suction pipette P attached with the suction tip C of this embodiment is operated again to transfer the collection of subjects M to another container. In this way, the selection accuracy of the selection subjects T1 can be improved if only the selection subjects T1 cannot be completely selected by one series of suction and discharge operations.

Further, a plurality of conical members may be provided in the suction tip C of this embodiment instead of performing the series of suction and discharge operations twice. For example, as another example of the suction tip C of this embodiment, another conical member may be arranged downstream of the passage hole 4 of the conical member 3 of this embodiment in the suction direction.

Even if the non-selection subjects T2 having passed through a passage hole of the other conical member at the time of suction flow in reverse through the passage hole of the other conical member at the time of discharge, a possibility that the non-selection subjects T2 also pass through the passage hole 4 of the conical member 3 provided at the upstream side is extremely low. The user can further improve the selection accuracy of the selection subjects T1.

Note that, to more reliably prevent a reverse flow of non-selection subjects in the case of providing a plurality of conical members, the user preferably arranges the passage holes of the respective conical members at non-coaxial positions in an axial direction of the tubular passage C1 of the suction tip C. By arranging the passage holes at such positions, even if the non-selection subjects T2 flow in reverse through the passage hole of another conical member arranged upstream of the conical member 3, the non-selection subjects T2 more easily precipitate to the storage portion 5 of the conical member 3 and a possibility that the non-selection subjects T2 pass through the passage hole 4 of the conical member 3 is extremely low.

Further, as shown in FIG. 2C, a sorting member D may be arranged downstream of the passage hole 4 of the conical member 3 to sort the non-selection subjects T2 having passed through the passage hole 4. In FIG. 2C, denoted by T2c1 are non-selection subjects sorted to the left and right by the sorting member D, and denoted by A1a are sorting directions. In this embodiment, the sorting member D is a conical member and arranged in an inverted manner such that an apex is located downstream of the passage hole 4. The sorting member D sorts a liquid flow including the non-selection subjects T2 having passed through the passage hole 4 in a circumferential direction by a conical inclined surface thereof and causes the liquid flow to move in a direction toward an inner wall of the tubular passage C1. The sorting member D is not particularly limited in shape and has only to be so shaped as to sort the non-selection subjects T2 having passed through the passage hole 4 in the direction toward the inner wall of the tubular passage C1 and may have, for example, a truncated pyramid shape or the like.

Figure 2D:
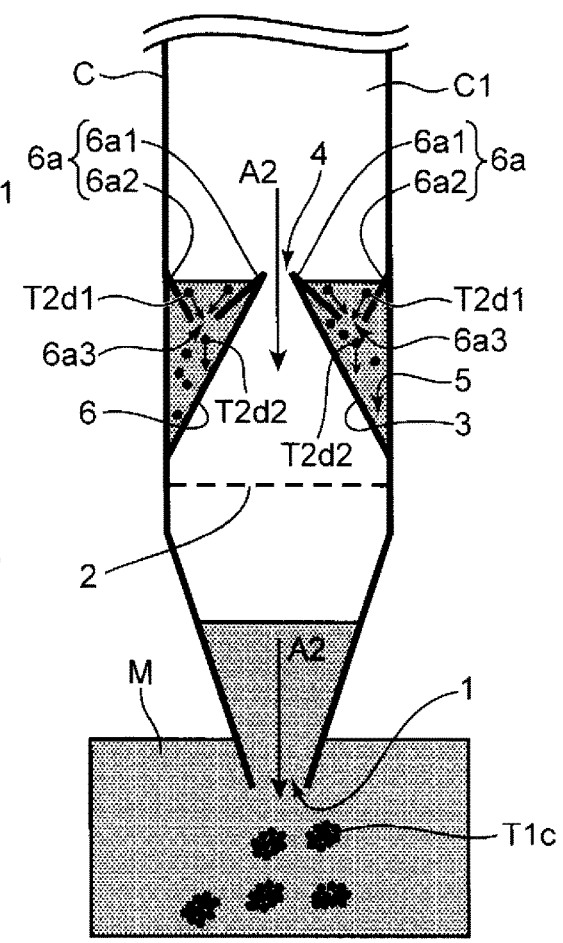
FIG. 2D is a diagram showing a discharge operation using the suction tip according to the other example of the first embodiment of the present disclosure.
Figure 2E:
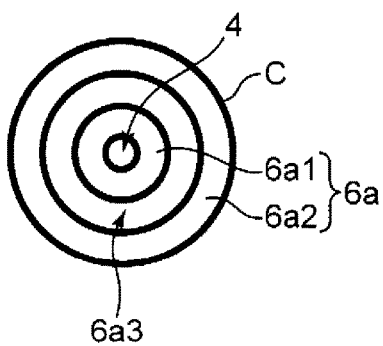
FIG. 2E is a plan view of the suction tip according to the other example of the first embodiment of the present disclosure.

Further, a reverse tapered portion 6a may be provided on at least one of a part of the outer peripheral wall of the conical member 3 and a part of the inner peripheral wall of the tubular passage C1. A case where the reverse tapered portion 6a is provided on both a part of the outer peripheral wall of the conical member 3 and a part of the inner peripheral wall of the tubular passage C1 is descried. The reverse tapered portion 6a is composed of an inner tapered piece 6a1 and an outer tapered piece 6a2 as shown in FIGS. 2D and 2E. FIG. 2D is a diagram showing a discharge operation using a suction tip according to another example of this embodiment, and FIG. 2E is a plan view of the suction tip according to the other example of this embodiment. The inner tapered piece 6a1 is a member joined to the outer peripheral wall of the conical member 3 on a downstream end part and extending around the outer peripheral wall of the conical member 3. The inner tapered piece 6a1 has an inclined surface for prompting the precipitation of non-selection subjects (non-selection subjects T2d1) at the time of discharge. The outer tapered piece 6a2 is a member joined to the inner peripheral wall of the tubular passage C1 on a downstream end part and extending around the inner peripheral wall of the tubular passage C1. The outer tapered piece 6a2 has an inclined surface for prompting the precipitation of non-selection subjects (non-selection subjects T2d1) at the time of discharge. A horizontal position of a joint part of the inner tapered piece 6a1 and the outer peripheral wall of the conical member 3 (upper edge part of the inner tapered piece 6a1) is substantially the same as that of a joint part of the outer tapered piece 6a2 and the inner peripheral wall of the tubular passage C1 (upper edge part of the outer tapered piece 6a2). An upstream end part of the inner tapered piece 6a1 and that of the outer tapered piece 6a2 are proximate to each other to form an annular passage hole 6a3. At the time of discharge, the non-selection subjects T2 pass through the passage hole 6a3 and precipitate to the storage portion 5 by having a flow passage therefor narrowed by the inner and outer tapered pieces 6a1, 6a2. Denoted by T2d2 are non-selection subjects having passed through the passage hole 6a3. By providing the reverse tapered portion 6a, the non-selection subjects T2 can be prompted to precipitate to the storage portion 5 and a reverse flow of the non-selection subjects T2 precipitated to the storage portion 5 can be more reliably prevented.

Second Embodiment

A suction tip Ca of a second embodiment of the present disclosure is described in detail below with reference to the drawings. FIGS. 3A through 3D are diagrams showing suction and discharge operations using the suction tip Ca of the second embodiment of the present disclosure, wherein FIG. 3A is a diagram showing a state of sucking a collection of subjects M when the collection of subjects M is sucked using the suction tip Ca of this embodiment and FIG. 3B is a diagram showing a state of discharging the collection of subjects M when the collection of subjects M is discharged using the suction tip Ca of this embodiment.

The suction tip Ca of the second embodiment is similar to the suction tip C of the first embodiment except for further including a valve mechanism 7 and a second film filter 8 (second selector) downstream of a passage hole 4 in a suction direction of the collection of subjects M. Thus, only points of difference are described.

Valve Mechanism 7

The valve mechanism 7 is arranged proximately to the passage hole 4 and is provided for the purpose of making flow paths for the collection of subjects M different between the time of suction and the time of discharge to more reliably capture non-selection subjects in a storage portion. As shown in FIG. 3A, the valve mechanism 7 includes a path for dividing non-selection subjects T2c having passed through the passage hole 4 to flow toward an outer peripheral side of the passage hole 4 (in directions of arrows A4) and move the non-selection subjects T2c toward the second film filter 8 before an upstream opening 7b of the valve mechanism at the time of sucking the collection of subjects M. Further, as shown in FIG. 3B, the valve mechanism 7 introduces liquid components included in the collection of subjects M having passed through the second film filter 8 into a main portion 7a of the valve mechanism 7 through a downstream opening 7c of the valve mechanism (in directions of arrows A6) and causes them to be discharged from the passage hole 4 at the time of discharging the collection of subjects M. The valve mechanism 7 includes the main portion 7a having a passage inside, the upstream and downstream openings 7b, 7c provided in the main portion 7a, and a lid portion 7d.

The main portion 7a includes the inner passage through which the liquid components included in the collection of subjects M pass at the time of discharge. The main portion 7a vertically moves in a tubular passage C1 according to the flow of the collection of subjects M when the collection of subjects M is sucked and discharged. The main portion 7a includes upper and lower openings.

A material for the main portion 7a is not particularly limited and resin such as polypropylene or polystyrene can be, for example, adopted as such. Besides, metal, such as aluminum, may be formed into the main portion 7a.

The upstream opening 7b is an opening on one end of the main portion 7a, and an opening area thereof is smaller than that of the passage hole 4 of a conical member 3. Further, the downstream opening 7c is an opening on the other end of the main portion 7a.

When the collection of subjects M is sucked, the main portion 7a moves in a suction direction as shown in FIG. 3A. Thus, the upstream opening 7b is separated from the passage hole 4 of the conical member 3. Further, the downstream opening 7c is held in contact with the lid portion 7d to be described later, thereby being closed. Thus, the collection of subjects M including the non-selection subjects T2 are divided to flow toward the outer peripheral side of the passage hole 4 (directions of arrows A4) before the upstream opening 7b without flowing into the main portion 7a through the upstream opening 7b.

On the other hand, when the collection of subjects M is discharged, the main portion 7a moves in a discharge direction as shown in FIG. 3B. Thus, a tip part of the upstream opening 7b enters the passage hole 4 of the conical member 3 to allow communication between the inner passage of the main portion 2a and an upstream area of the passage hole 4 of a tapered portion 6. Further, the downstream opening 7c is separated from the lid portion 7d to be described later by a movement of the main portion 7a, thereby being opened. Thus, the collection of subjects M including the non-selection subjects T2 is introduced into the main portion 7a through the opened downstream opening 7c (directions of arrows A6) and discharged to the upstream area of the passage hole 4 through the upstream opening 7b. At this time, the non-selection subjects T2d stored in the tapered portion 6 do not join the collection of subjects M being discharged.

An opening area of the upstream opening 7b is not particularly limited and has only to be a size which enables the entrance of the tip part into the aforementioned passage hole 4. For example, if the opening area of the passage hole 4 is 7500 to 200000 $\mu m^2$, that of the upstream opening 7b can be about 3500 to 100000 $\mu m^2$.

The shape of a tip including the upstream opening 7b is narrowed in diameter toward the upstream side so that the opening area is smaller than a cross-sectional area of the main portion 7a as shown in FIG. 3B. Thus, when the main portion 7a moves toward the upstream side at the time of discharge, the tip part thereof including the upstream opening 7b easily enters the passage hole 4 and the collection of subjects M introduced into the main portion 7a through the downstream opening 7c is easily discharged from the upstream opening 7b.

As shown in FIG. 3A, the lid portion 7d comes into contact with the downstream opening 7c of the main portion 7a moved toward the upstream side to close the downstream opening 7c when the collection of subjects M is sucked. On the other hand, as shown in FIG. 3B, the lid portion 7d is separated from the downstream opening 7c to open the downstream opening 7c since the main portion 7a moves toward the upstream side when the collection of subjects M is discharged.

A material for the lid portion 7d is not particularly limited and resin such as polypropylene or polystyrene can be, for example. Besides, metal, such as aluminum, may be formed into the lid portion 7d. The lid portion 7d is held in contact with the downstream opening 7c as described above to close the downstream opening 7c. Thus, the lid portion 7d is preferably made of a resin material with a sealing property.

The second film filter 8 is provided on the outer periphery of the valve mechanism 7.

Second Film Filter 8

The second film filter 8 permits the passage of only liquid components constituting the collection of subjects M out of the collection of subjects M including the non-selection subjects T2 without permitting the passage of the non-selection subjects T2.

As shown in FIG. 3A, the second film filter 8 is provided between the upstream opening 7b and the downstream opening 7c. Specifically, the second film filter 8 is a doughnut-shaped film body, the outer peripheral edge thereof is joined to an inner peripheral wall of the tubular passage C1, and the inner peripheral edge thereof is joined to an outer peripheral wall of the main portion 7a of the valve mechanism 7. Further, the second film filter 8 is provided in a suction path through which the collection of subjects M having passed through the passage hole 4 of the tapered portion 6 passes at the time of suction.

Note that although the second film filter 8 is provided between the upstream opening 7b and the downstream opening 7c in this embodiment, the position thereof is not particularly limited to this position. Another example of the position of the second film filter 8 is described in detail later.

The second film filter 8 is a porous film provided with through holes (second through holes) having a smaller diameter than those of the non-selection subjects T2. An opening area of the second through holes is not particularly limited. The user can adopt the second film filter 8 provided with the second through holes having an optimal opening area in accordance with the diameters of the non-selection subjects T2 to be selected. As an example, the diameter of the second through holes of the second film filter 8 can be set at about 10 μm when the non-selection subjects T2 are cells having a diameter of 20 μm. The thickness of the second film filter 8 is not particularly limited and is, for example, about 5 to 20 μm. As just described, the second film filter 8 is not bulky due to a small thickness thereof and can be provided in a suction pipette. Further, an inner volume is not drastically reduced even as compared with a suction tip including no second film filter 8. Thus, a measurement error due to a difference in inner volume does not occur in the case of using a conventional suction tip or the suction tip C of the first embodiment provided with the second film filter 8.

The type of the second film filter 8 is not particularly limited and one similar to the first film filter 2 described above can also be adopted. Further, the shape of the second through holes is also not particularly limited and that similar to the first through holes of the first film filter 2 described above can be adopted.

The operation of the valve mechanism 7 in the case of suction and discharge using the suction tip Ca of this embodiment is described below.

As shown in FIG. 3A, the main portion 7a of the valve mechanism 7 moves in the suction direction of the collection of subjects M when the user sucks the collection of subjects M by operating the suction pipette or the like (not shown) as a suction device. An arrow A3 indicates a moving direction of the main portion 7a. The downstream opening 7c comes into contact with the lid portion 7d due to a movement of the main portion 7a, thereby being closed.

As described above, when the downstream opening 7c is closed by the lid portion 7d, air originally present in the inner passage of the main portion 7a and the collection of subjects M introduced into the inner passage of the main portion 7a in an initial stage of suction are not discharged from the downstream opening 7c. Thus, the newly sucked collection of subjects M cannot enter the inner passage of the main portion 7a. As a result, the collection of subjects M does not flow into the main portion 7a through the upstream opening 7b and is divided to flow toward the outer peripheral side of the passage hole 4 (directions of arrows A4) before the upstream opening 7b. The collection of subjects M including the non-selection subjects T2 reaches the second film filter 8 by the user continuing suction. As described above, the second film filter 8 permits the passage of only the liquid components constituting the collection of subjects M without permitting the passage of the non-selection subjects T2. Denoted by T2e are non-selection subjects staying near the second film filter 8 without being able to pass through the second film filter 8.

As shown in FIG. 3B, the main portion 7a of the valve mechanism 7 moves in the discharge direction of the collection of subjects M when the user discharges the collection of subjects M by operating the suction pipette or the like as a suction device. An arrow A5 indicates a moving direction of the main portion 7a. The downstream opening 7c is separated from the lid portion 7d, with which the downstream opening 7c has been in contact, thereby being opened. The tip part including the upstream opening 7b enters the passage hole 4 of the conical member 3. As a result, the liquid components constituting the collection of subjects M having passed through the second film filter 8 flow into the main portion 7a through the downstream opening 7c (directions of arrows A6), pass through the interior of the main portion 7a and are discharged through the upstream opening 7b in a direction of an arrow A2.

The non-selection subjects T2e staying near the second film filter 8 precipitate to the storage portion 5 by gravity when the user finishes the suction. At the time of discharge, the tip part of the main portion 7a of the valve mechanism 7 enters the passage hole 4 to close the passage hole 4 before the non-selection subjects T2 reach the passage hole 4 from the vicinity of the second film filter 8. Thus, there is no likelihood that the non-selection subjects T2 flow in reverse through the passage hole 4 to be discharged.

As described above, the suction tip Ca of this embodiment includes the valve mechanism 7 and the second film filter 8. The valve mechanism 7 moves the main portion 7a to cause the tip part of the upstream opening 7b to enter the passage hole 4 and close the passage hole 4 at the time of discharge. Thus, the suction tip Ca of this embodiment can prevent the floating non-selection subjects T2 from flowing in reverse through the passage hole 4 and joining the selection subjects T1 even if the non-selection subjects T2 not stored in the storage portion 5 are floating in the collection of subjects M.

Further, since the tip part including the upstream opening 7b and the passage hole 4 of the conical member 3 communicate at the time of discharge in the suction tip Ca of this embodiment, only the liquid components of the collection of subjects M having passed through the second film filter 8 are permitted to pass through the passage hole 4 and discharged together with the selection subjects T1 selected by the first film filter 2. As a result, only the selection subjects T1 can be more reliably selected from the collection of subjects M and discharged only by performing a series of suction and discharge operations.

Note that although the conical member 3 is used as a capture mechanism (capture portion) and the storage portion 5 is formed between the outer peripheral wall of the tapered portion 6 of the conical member and the inner peripheral wall of the tubular passage C1 in this embodiment, a storage mode for the non-selection subjects T2 is not particularly limited.

For example, as shown in FIGS. 3C and 3D, a saucer-shaped member S provided downstream of the first film filter 2 can be adopted as the capture mechanism. The saucer-shaped member S is circular and includes an opening hole Sa and a wall portion Sa1 provided around the opening hole Sa. As shown in FIG. 3C, the non-selection subjects T2b pass through the opening hole Sa at the time of discharge. A movement of the non-selection subjects having passed through is blocked by the second film filter 8. Thereafter, the non-selection subjects (non-selection subjects T2e1) precipitate to a saucer of the saucer-shaped member S. The wall portion Sa1 is provided to cause the non-selection subjects T2e1 precipitated to the saucer-shaped member S to be stably stored. As described above, the valve mechanism 7 moves to the upstream side at the time of discharge. As a result, the tip part including the upstream opening 7b has a part of the outer periphery thereof held in contact with the wall portion Sa and enters the opening hole Sa to close the opening hole Sa. As a result, the non-selection subjects T2b do not reversely flow through the opening hole Sa.

Note that although the wall portion Sa1 is provided around the opening hole Sa in FIGS. 3C and 3D, the wall portion Sa is not essential.

Further, although the suction tip Ca integrally provided with the second film filter 8 and the valve mechanism 7 is described as an example in this embodiment, the second film filter 8 and the valve mechanism 7 can be prepared as separate members. Specifically, a filter unit provided with the second film filter 8 and a unit provided with the valve mechanism 7 may be prepared and a suction tip unit connectable to these units may be prepared. The prepared units can be easily assembled into the suction tip Ca of this embodiment by being configured to be bondable or fittable. Further, according to need, only a part of the valve mechanism 7 may be provided as a unit or a part of the valve mechanism 7 may be integrally provided to the second film filter 8. Specifically, only the lid portion 7d of the valve mechanism 7 may be integrally provided to the suction tip Ca and a unit in which the outer peripheral wall of the main portion 7a is joined to the second film filter may be prepared. Besides, a hole in which the main portion 7a of the valve mechanism 7 is movable may be provided in a central part of the second film filter 8 and the valve mechanism 7 may be configured to be vertically movable at the time of suction and discharge.

Third Embodiment

Figure 4:
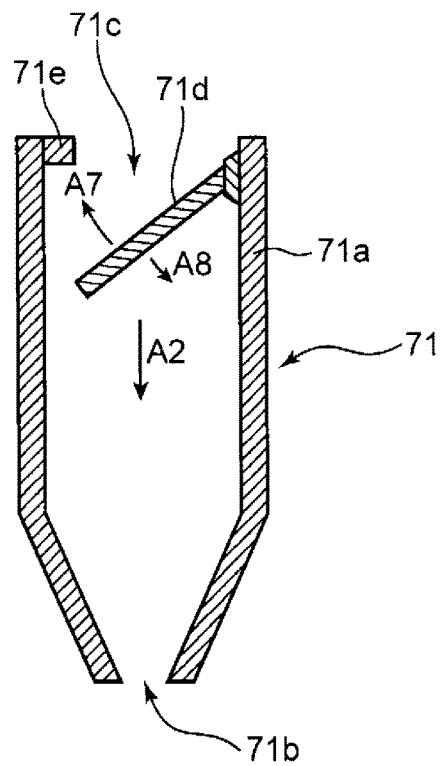
FIG. 4 is a diagram showing the operation of a valve mechanism of a suction tip according to a third embodiment of the present disclosure.

A suction tip of a third embodiment of the present disclosure is described in detail below with reference to the drawing. FIG. 4 is a diagram showing the operation of a valve mechanism 71 of the suction tip according to the third embodiment of the present disclosure.

The suction tip of the third embodiment is similar to that of the second embodiment except in the structure and operation of the valve mechanism 71. Thus, only points of difference are described.

Valve Mechanism 71

As shown in FIG. 4, the valve mechanism 71 has a swing type check valve mechanism. The valve mechanism 71 is composed of a main portion 71a, an upstream opening 71b, a downstream opening 71c and a lid portion 71d. Components of the valve mechanism 71 other than the lid portion 71d are not described since being configured similarly to those of the valve mechanism 7 described in the second embodiment.

One end of the lid portion 71d is rotatably attached to an inner peripheral wall of the main portion 71a near the downstream opening 71c.

A method for rotatably attaching one end of the lid portion 71d to the inner peripheral wall of the main portion 71a is not particularly limited. For example, the lid portion 71d and the inner peripheral wall of the main portion 71a can be rotatably attached using a hinge.

The lid portion 71d operates as follows at the time of sucking and discharging a collection of subjects M.

Specifically, in performing a suction operation, a user normally discharges air in a tubular passage C1 of a suction tip C such as by pushing a push button (not shown) of a suction pipette P (see FIG. 1) as a suction device with the suction tip C attached to a tip part of the suction pipette P. If the suction of the collection of subjects M through a tip opening 1 of the suction tip C is started in this state, air flows in a suction direction of the collection of subjects M in an inner passage of the main portion 71a of the valve mechanism 71 in an initial stage of suction. By this flow of the air, the lid portion 71d rotates in a direction to come into contact with a contact portion 71e (direction of an arrow A7) and comes into contact with the contact portion 71e to close the downstream opening 71c.

The contact portion 71e is a member projecting from an inner peripheral wall of the inner passage of the main portion 71a and provided near the downstream opening 71c. The contact portion 71e stops the rotation of the lid portion 71d by coming into contact with the rotating lid portion 71d. A projecting length of the contact portion 71e that comes into contact with the rotating lid portion 71d is not particularly limited and has only to be sufficient to cause an end part of the rotating lid portion 71d to come into contact.

When the downstream opening 71c is closed by the lid portion 71d, the air and the collection of subjects M present in the inner passage of the main portion 71a cannot move in the suction direction and stay in the inner passage of the main portion 71a. As a result, newly sucked air and collection of subjects M do not flow into the inner passage of the main portion 71a and are divided to flow toward an outer peripheral side of the passage hole 4 (directions of arrows A4, see FIG. 3A) before the upstream opening 71b of the valve mechanism 71.

On the other hand, at the time of discharge, the main portion 71a moves and the tip part including the upstream opening 71b enters the passage hole 4 of the conical member 3 (see FIG. 3B) as described in the second embodiment. Liquid components constituting the collection of subjects M (see FIG. 3B) flow in the direction of the arrow A2 and push the lid portion 71d open, thereby rotating the lid portion 71d in a direction to open the downstream opening 71c (direction of an arrow A8). The liquid components constituting the collection of subjects M flow into the inner passage of the main portion 71a through the opened downstream opening 71c and are discharged through the upstream opening 71b.

Note that although the lid portion 71d rotated by the flow of the collection of subjects M is illustrated in this embodiment, the lid portion 71d is not limited to this. For example, an elastic member such as a compression spring may be attached to the lid portion 71d to constantly close the downstream opening 71c at the time of suction and in a state before suction. In this case, a stress applied to the lid portion 71d (stress in the direction of the arrow A7) by the elastic member such as a compression spring is set to be smaller than a stress applied to the lid portion 71d (stress in the direction of the arrow A8) to open the downstream opening 71c by the flow of the collection of subjects M at the time of discharge.

Note that a sealing material is preferably provided at a position where the lid portion 71d and the contact portion 71e are in contact to more reliably close the downstream opening 71c. The sealing material is not particularly limited and a sealing material such as natural rubber, synthetic rubber or Teflon (registered trademark) nonstick coating can be adopted.

Fourth Embodiment

Figure 5:
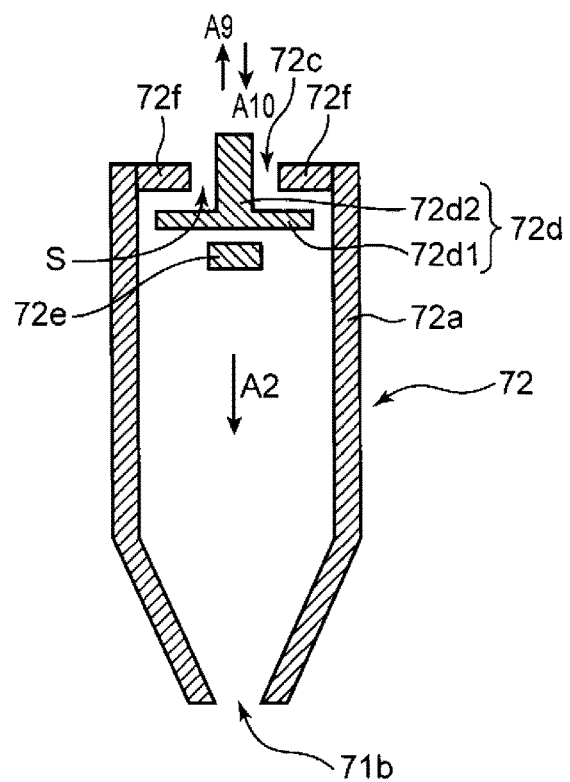
FIG. 5 is a diagram showing the operation of a valve mechanism of a suction tip according to a fourth embodiment of the present disclosure.

A suction tip of a fourth embodiment of the present disclosure is described in detail below with reference to the drawing. FIG. 5 is a diagram showing the operation of a valve mechanism 72 of the suction tip according to the fourth embodiment of the present disclosure.

The suction tip of the fourth embodiment is similar to that of the second embodiment except in the structure and operation of the valve mechanism 72. Thus, only points of difference are described.

Valve Mechanism 72

As shown in FIG. 5, the valve mechanism 72 has a lift type check valve mechanism. The valve mechanism 72 is composed of a main portion 72a, an upstream opening 72b, a downstream opening 72c and a lid portion 72d. Components of the valve mechanism 72 other than the lid portion 72d are not described since being configured similarly to those of the valve mechanism 7 described in the second embodiment.

The lid portion 72d is vertically movably provided near the downstream opening 72c. The lid portion 72d is composed of a substantially disk-shaped lid main body 72d1 and a shaft 72d2 connected to the lid main body 72d1.

The lid main body 72d1 has such a cross-sectional shape as to cover the downstream opening 72c. Further, a diameter of a cross-section of the lid main body 72d1 is smaller than an inner diameter of an inner passage of the main portion 72a. Thus, the lid portion 72d can vertically move in the inner passage of the main portion 72a and close the downstream opening 72c.

The shaft 72d2 is a member which functions as a guide when the lid portion 72d vertically moves (directions of arrows A9 and A10) in the inner passage of the main portion 72a.

At the time of discharge to be described later, liquid components included in a collection of subjects M flow into the inner passage of the main portion 72a through the downstream opening 72c. Thus, a diameter of the shaft 72d2 is smaller than an opening area of the downstream opening 72c so as to be able to form such a clearance S that the liquid components of the collection of subjects M can sufficiently pass through the downstream opening 72c.

The shaft 72d2 may be integrally formed to the lid main body 72d1 or may be integrally formed by joining or the like after being prepared as a separate body.

As described in detail in the third embodiment, a user discharges air in the inner passage of the suction tip such as by pushing a push button of a suction pipette (not shown) as a suction device with the suction tip attached to a tip part of the suction pipette when performing a suction operation.

If the suction of the collection of subjects M through a suction port of the suction tip is started in this state, air flows in a suction direction of the collection of subjects M in the inner passage of the main portion 72a of the valve mechanism 72 in an initial stage of suction. By this flow of the air, the lid portion 72d moves upward (direction of the arrow A9) and comes into contact with a contact portion 72f to close the downstream opening 72c.

The contact portion 72f is a member projecting in the inner passage of the main portion 72a and provided near the downstream opening 72c. The contact portion 72f stops the movement of the lid portion 72d by coming into contact with the lid portion 72d moving upward. A projecting length of the contact portion 72f is not particularly limited and has only to be sufficient to cause an end part of the lid main body 72d1 to come into contact.

On the other hand, at the time of discharge, the main portion 72a moves and the tip part including the upstream opening 72b enters the passage hole 4 of the conical member 3 (see FIG. 3B) as described in the second embodiment. The liquid constituting the collection of subjects M (see FIG. 3B) flows in a discharge direction (direction of the arrow A2) to move the lid portion 72d downward (direction of the arrow A10). The liquid components constituting the collection of subjects M flow into the inner passage of the main portion 72a through the clearance S of the downstream opening 72c opened by the movement of the lid portion 72d and are discharged from the upstream opening 72b. Note that the lid portion 72d moving downward (direction of the arrow A10) comes into contact with a contact portion 72e to be stopped.

The contact portion 72e stops the movement of the lid portion 72d by coming into contact with the downward moving lid portion 72d. The contact portion 72e is a member projecting in a part of the inner passage of the main portion 72a.

Note that a sealing material is preferably provided at a position where the end part of the lid portion 72d and the contact portion 72f are in contact to more reliably close the downstream opening 72c. The sealing material is not particularly limited and a sealing material such as natural rubber, synthetic rubber or Teflon (registered trademark) nonstick coating can be adopted.

Although the valve mechanism 72 provided with the lid main body 72d1 having such a cross-sectional shape as to cover the downstream opening 72c is illustrated in this embodiment, the cross-sectional shape of the lid main body 72d1 is not particularly limited. For example, a lid portion 72d shaped similarly to the conical member 3 described in detail in the first embodiment may be adopted and an engaging surface to be closely engaged with the tapered portion 6 of the conical member 3 may be provided on the contact portion 72f.

Figure 6:
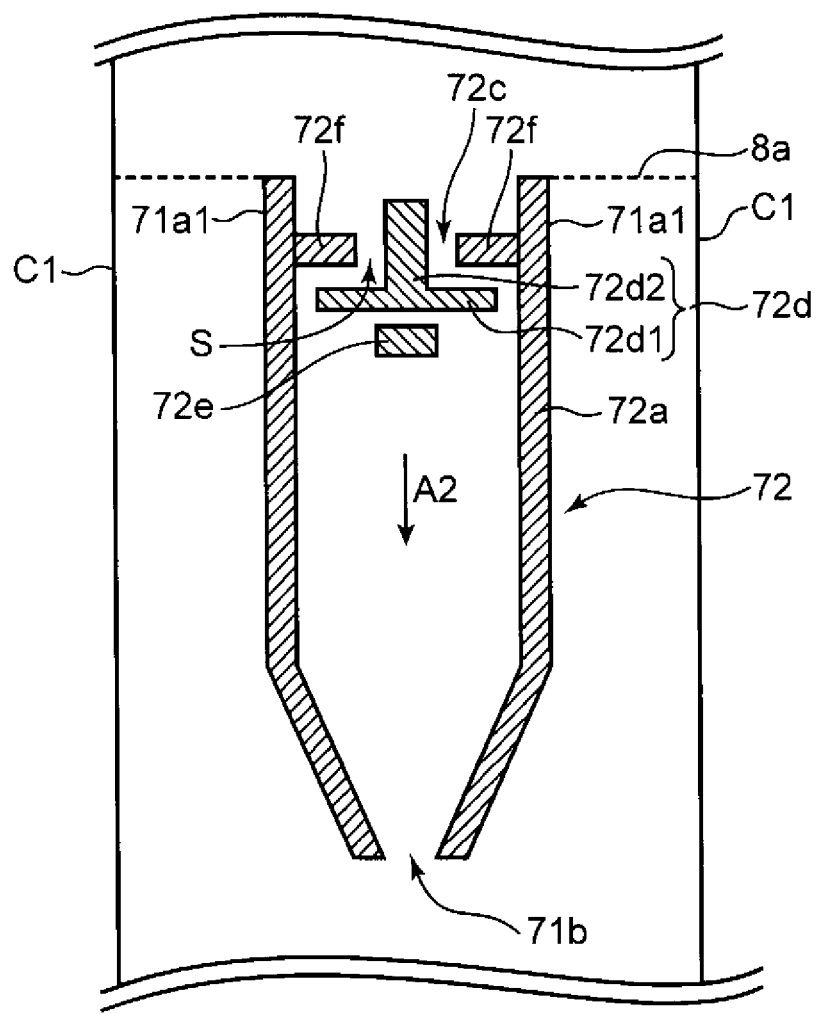
FIG. 6 is a diagram showing another example of the valve mechanism of the suction tip according to the fourth embodiment of the present disclosure.

Further, the position of the second film filter 8 is not limited to the one between the upstream opening and the downstream opening as described in the second embodiment. For example, as shown in FIG. 6, a second film filter (second film filter 8a) may be provided between a part of an extending portion 71a1 and the upstream opening 71b when the extending portion 71a1 is provided on a part of the main portion 71a. In this case, the outer peripheral edge of the second film filter 8 is joined to an outer peripheral wall of the extending portion 71a1 and the inner peripheral edge thereof is joined to an outer peripheral wall of the extending portion 71a1. Specifically, the second film filter 8a has only to be located at such a position that the liquid components of the collection of subjects having passed through the second film filter 8a at the time of suction can pass through the interior of the main portion 71a of the valve mechanism 7 without being mixed with the non-selection subjects at the time of discharge.

Fifth Embodiment

A suction tip of a fifth embodiment of the present disclosure is similar to that of the fourth embodiment except in the structure and operation of a valve mechanism 73. Thus, only points of difference are described.

Figure 7B:
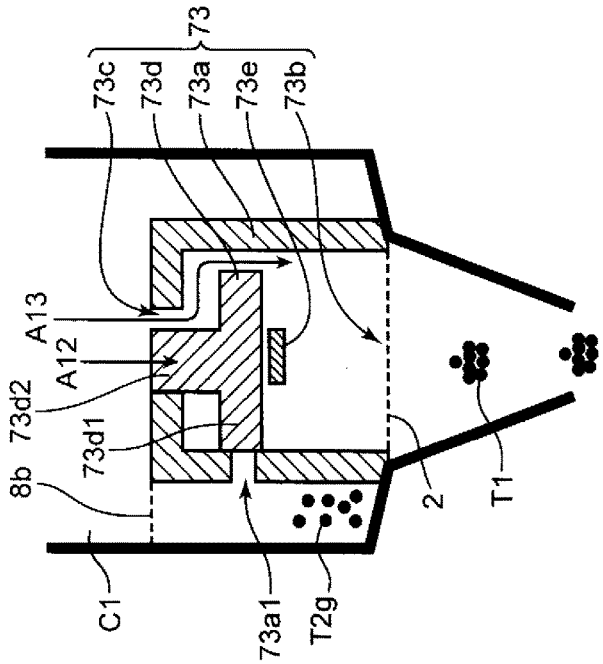
FIG. 7 is a diagram of a valve mechanism of a suction tip according to a fifth embodiment of the present disclosure.
Figure 7D:
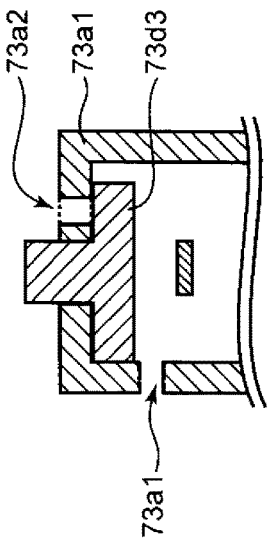
Figure 7A:
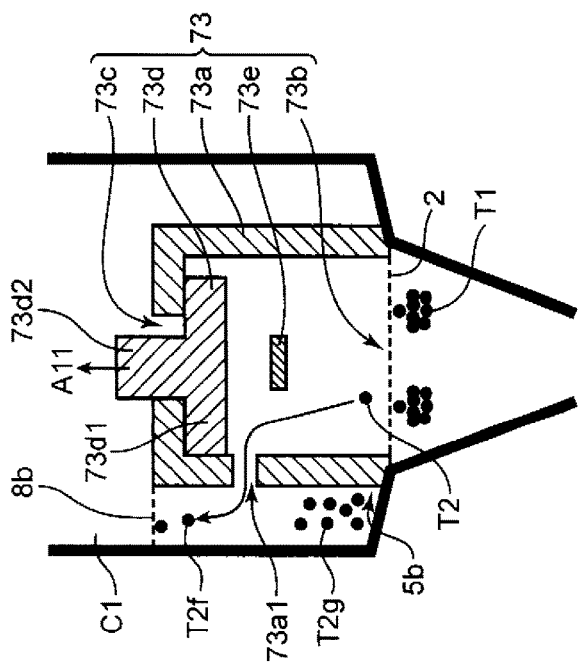

As shown in FIG. 7A, the valve mechanism 73 of the suction tip of this embodiment includes a main portion 73a, an upstream opening 73b, a downstream opening 73c and a lid portion 73d. The lid portion 73d is composed of a lid main body 73d1 and a shaft 73d2 connected to the lid main body 73d1. A contact portion 73e has the same functions as the contact portion 72e described above in the fourth embodiment.

The main portion 73a of the valve mechanism 73 of this embodiment is joined to an inner wall of a tubular passage C1 at a downstream side of a first film filter 2. Further, a passage hole 73a1 is formed in a side peripheral wall of the main portion 73a. A storage portion 5b is a space formed between an outer peripheral wall of the main portion 73a and an inner peripheral wall of the tubular passage C1.

At the time of suction, the lid portion 73*d* moves to a downstream side to close the downstream opening 73*c* and open the passage hole 73*a*1 as shown in FIG. 7A. An arrow A11 indicates a moving direction of the lid portion 73*d* at the time of suction. Non-selection subjects T2 having passed through the first film filter 2 pass through the passage hole 73*a*1. Denoted by T2*f* are non-selection subjects having passed through the passage hole 73*a*1. A second film filter 8*b* does not permit the passage of the non-selection subjects T2*f*.

A diameter of the lid main body 73*d*1 of the lid portion 73*d* is set to be smaller than an inner diameter of an inner passage of the main portion 73*a* so that liquid components flowing in through the downstream opening 73*c* pass through the interior of the main portion 73*a* and are discharged at the time of discharge.

Thus, at the time of discharge, the lid portion 73*d* moves to an upstream side to open the downstream opening 73*c* and close the passage hole 73*a*1 with a side surface of the lid main body 73*d*1 as shown in FIG. 7B. An arrow A12 indicates a moving direction of the lid portion 73*d* at the time of discharge. The liquid components having passed through the second film filter 8*b* are introduced through the opened downstream opening 73*c* and discharged from the upstream opening 73*b*. Further, the non-selection subjects T2*f* precipitate to the storage portion 5*b*. As described above, since the passage hole 73*a*1 is closed at the time of discharge, the non-selection subjects T2*g* do not flow in reverse through the passage hole 73*a*1.

Note that although the passage hole 73*a*1 is provided in a lateral direction in this embodiment, a formation direction of the passage hole 73*a*1 is not particularly limited. For example, the passage hole 73*a*1 may be provided in a direction inclined downward from the inner periphery to the outer periphery of the main portion 73*a*. In this case, the non-selection subjects T2*f* having passed through the passage hole 73*a*1 and reached the second film filter 8*b* are unlikely to flow in reverse when precipitating to the storage portion 5.

Figure 7C:
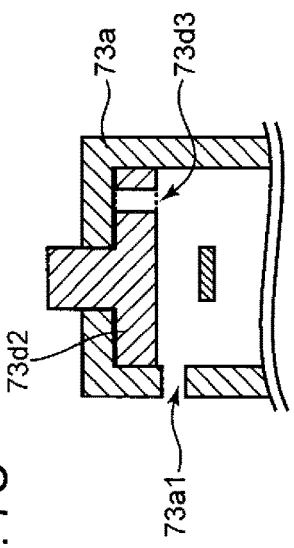

Further, although the liquid components having passed through the second film filter 8*b* pass through the downstream opening 73*c* at the time of discharge in this embodiment as shown in FIG. 7B, a discharge path for the liquid components is not particularly limited. For example, a through hole 73*d*3 vertically penetrating through the lid main body (lid main body 73*d*2) may be provided as a discharge path for the liquid components in the lid main body 73 as show in FIG. 7C and the liquid components may pass through this through hole 73*d*3. Since a downstream opening of the through hole 73*d*3 is in contact with the inner periphery of the main portion 73*a* at the time of suction as shown in FIG. 7C, the non-selection subjects pass through the passage hole 73*a*1.

Furthermore, as shown in FIG. 7D, a through hole 73*a*2 penetrating through the main portion 73*a* may be provided in a part (e.g. upper surface portion) of the main portion 73*a* and the liquid components may pass through this through hole 73*a*2. Since an upstream opening of the through hole 73*a*2 is in contact with the lid main body 73*d*3 at the time of suction, the non-selection subjects pass through the passage hole 73*a*1.

Note that disclosures having the following configurations are mainly included in the specific embodiments described above.

A suction tip according to one aspect of the present disclosure includes a tip opening configured to suck or discharge a collection of subjects including selection subjects and non-selection subjects, a tubular passage provided with a first selector configured to select the selection subjects and the non-selection subjects included in the collection of subjects sucked through the tip opening and permit the passage of the non-selection subjects, and a capture portion provided on a side of the tubular passage downstream of the first selector in a suction direction of the collection of subjects and configured to capture the non-selection subjects, and the capture portion includes a passage hole configured to permit the passage of the non-selection subjects and a storage portion configured to store the non-selection subjects having passed through the passage hole.

According to the present disclosure, by adopting such a configuration, only impurities having a diameter smaller than a desired diameter are permitted to pass through the passage hole of the capture portion and are stored in the storage portion at the time of suction. As a result, only the selection subjects having a large diameter can be discharged by performing only a series of simple operations including suction and discharge. Since these operations do not require an operation of removing the capture portion such as a filter, contamination does not occur before and after the operations.

The first selector is preferably a film filter including a plurality of through holes in a surface thereof.

According to the present disclosure, by adopting such a configuration, the suction tip does not become bulky even if the film filter is mounted therein. Further, if film filters including holes with various hole diameters are prepared and a film filter is selected according to the shapes of selection subjects, the selection subjects having various shapes can be selected.

Preferably, the capture portion includes a tapered portion for narrowing a flow passage for the sucked subjects toward a downstream side in the suction direction of the collection of subjects and the passage hole is formed in a narrowed end part of the tapered portion.

According to the present disclosure, by adopting such a configuration, the non-selection subjects having passed through the first selector are easily introduced to the passage hole. As a result, the non-selection subjects are easily stored in the storage portion after passing through the passage hole and the selection capability of the suction tip can be improved.

Preferably, the tubular passage is a passage provided with an inner peripheral wall having a substantially circular cross-section, the capture portion is a conical member whose upstream end part in the suction direction of the collection of subjects is joined to the inner peripheral wall and which is formed with the passage hole on a downstream side in the suction direction of the collection of subjects, and the storage portion is a space formed between an outer peripheral wall of the conical member of the capture portion and the inner peripheral wall of the tubular passage.

According to the present disclosure, by adopting such a configuration, the non-selection subjects are easily introduced to the passage hole at the time of sucking the collection of subjects while being easily introduced to the storage portion along the outer peripheral wall of the conical member at the time of discharging the collection of subjects. Thus, the non-selection subjects can be efficiently removed.

Preferably, a valve mechanism provided on a side of the tubular passage downstream of the passage hole in the suction direction of the collection of subjects and a second selector are further provided. The valve mechanism includes a main portion with a passage inside, an upstream opening provided on an upstream side of the main portion in the suction direction of the collection of subjects, a downstream opening provided on a downstream side of the main portion in the suction direction of the collection of subjects, and a lid portion configured to close the downstream opening at the time of sucking the collection of subjects and open the downstream opening at the time of discharging the collection of subjects. The second selector is provided downstream of the upstream opening and upstream of the downstream opening and permits the passage of the collection of subjects while selecting the non-selection subjects from the collection of subjects having passed through the passage hole.

According to the present disclosure, by adopting such a configuration, it can be prevented that the floating non-selection subjects flow in reverse and join the selection subjects when the non-selection subjects not stored in the storage portion despite the passage through the passage hole are floating in the collection of subjects.

Preferably, the lid portion comes into contact with the downstream opening of the main portion moving to the downstream side in the suction direction of the collection of subjects to close the downstream opening at the time of sucking the collection of subjects, and the main portion moves to the upstream side in the suction direction of the collection of subjects to open the closed downstream opening and causes a tip part including the upstream opening to enter the passage hole of the capture portion to discharge the collection of subjects having passed through the second selector through the upstream opening at the time of discharging the collection of subjects.

According to the present disclosure, by adopting such a configuration, the tip part including the upstream opening and the passage hole of the capture portion communicate at the time of discharge, thereby blocking a path for permitting the non-selection subjects not having passed through the second selector to pass through the passage hole. Thus, the selection capability of the suction tip can be improved.

The selection subjects are preferably bio-based cells.

According to the present disclosure, by adopting such a configuration, a contribution can be made in operation efficiency in the fields of bio-related technology and medicine in which contamination is particularly problematic.

The selection subjects are preferably bio-based cell aggregates.

According to the present disclosure, by adopting such a configuration, a test result considering functions of individual cells can be obtained as compared with a test result obtained using one cell, and experiment conditions can be made uniform in accordance with an environment in a biological body. Further, since only cell aggregates having a predetermined shape can be selected out of cell aggregates having various shapes, the suction tip can obtain a highly reliable result in the fields of bio-related technology and medicine.

The invention claimed is:

1. A suction tip, comprising:
a tip opening configured to suck or discharge a collection of subjects including selection subjects and non-selection subjects;
a tubular passage provided with a first selector configured to select the selection subjects and the non-selection subjects included in the collection of subjects sucked through the tip opening and permit the passage of the non-selection subjects; and
a capture portion provided on a side of the tubular passage downstream of the first selector in a suction direction of the collection of subjects and configured to capture the non-selection subjects,
wherein the capture portion includes:
a tapered portion for narrowing a flow passage for the sucked collection of subjects toward a downstream side in the suction direction of the collection of subjects,
a passage hole configured to permit the passage of the non-selection subjects; the passage hole being formed at a downstream end of the tapered portion in the suction direction and
a storage portion configured to store the non-selection subjects having passed through the passage hole, the storage portion being formed between an outer peripheral wall of the tapered portion and an inner peripheral wall of the tubular passage, and
the tip opening and the passage hole are coaxially arranged on a central axis of the tubular passage.

2. The suction tip according to claim 1, wherein the first selection means is a film filter including a plurality of through holes in a surface thereof.

3. The suction tip according to claim 1, wherein:
the tubular passage is a passage provided with an inner peripheral wall having a substantially circular cross-section;
the capture portion is a conical member whose upstream end part in the suction direction of the collection of subjects is joined to the inner peripheral wall and which is formed with the passage hole on a downstream side in the suction direction of the collection of subjects; and
the storage portion is a space formed between an outer peripheral wall of the conical member of the capture portion and the inner peripheral wall of the tubular passage.

4. The suction tip according to claim 1, wherein:
the selection subjects are bio-based cells.

5. The suction tip according to claim 4, wherein:
the selection subjects are bio-based cell aggregates.

6. A suction tip, comprising:
a tip opening configured to suck or discharge a collection of subjects including selection subjects and non-selection subjects;
a tubular passage provided with a first selector configured to select the selection subjects and the non-selection subjects included in the collection of subjects sucked through the tip opening and permit the passage of the non-selection subjects;
a capture portion provided on a side of the tubular passage downstream of the first selector in a suction direction of the collection of subjects and configured to capture the non-selection subjects,
wherein the capture portion includes:
a passage hole configured to permit the passage of the non-selection subjects; and
a storage portion configured to store the non-selection subjects having passed through the passage hole,
a valve mechanism provided on a side of the tubular passage downstream of the passage hole in the suction direction of the collection of subjects; and
a second selector, the valve mechanism includes:
  a main portion with a passage inside,
  an upstream opening provided on an upstream side of the main portion in the suction direction of the collection of subjects,
  a downstream opening provided on a downstream side of the main portion in the suction direction of the collection of subjects, and
  a lid portion configured to close the downstream opening at the time of sucking the collection of subjects and open the downstream opening at the time of discharging the collection of subjects; and
  the second selector is provided between the upstream opening and the downstream opening, and around the valve mechanism, and permits the passage of the collection of subjects while selecting the non-selection subjects from the collection of subjects having passed through the passage hole.

7. The suction tip according to claim 6, wherein:
the lid portion comes into contact with the downstream opening of the main portion moving to the downstream side in the suction direction of the collection of subjects to close the downstream opening at the time of sucking the collection of subjects; and
the main portion moves to the upstream side in the suction direction of the collection of subjects to open the closed downstream opening and causes a tip part including the upstream opening to enter the passage hole of the capture portion to discharge the collection of subjects having passed through the second selector through the upstream opening at the time of discharging the collection of subjects.

* * * * *